United States Patent [19]

Matsumoto et al.

[11] Patent Number: 4,652,673
[45] Date of Patent: * Mar. 24, 1987

[54] PROCESS FOR PRODUCING METHACRYLIC ACID

[75] Inventors: Mutsumi Matsumoto; Kouichi Wada, both of Takasaki, Japan

[73] Assignee: Nippon Kayaku Kabushiki Kaisha, Tokyo, Japan

[ * ] Notice: The portion of the term of this patent subsequent to Aug. 21, 2001 has been disclaimed.

[21] Appl. No.: 484,620

[22] Filed: May 18, 1983

Related U.S. Application Data

[63] Continuation of Ser. No. 130,130, Mar. 13, 1980, abandoned.

[30] Foreign Application Priority Data

Mar. 22, 1979 [JP] Japan .................................. 54-32323

[51] Int. Cl.$^4$ ..................... C07C 51/25; C07C 57/055
[52] U.S. Cl. .................................... 562/535; 562/534; 562/539; 562/547; 562/546; 502/209
[58] Field of Search ....................... 562/535, 538, 547; 252/435, 437; 502/209

[56] References Cited

U.S. PATENT DOCUMENTS 4,178,464 12/1979 Sakamoto et al. .................. 562/535
4,467,113 8/1984 Matsumoto et al. ................ 562/535

Primary Examiner—Werren B. Lone
Attorney, Agent, or Firm—Henry C. Nields

[57] ABSTRACT

A process for producing methacrylic acid by vapor phase oxidation of methacrolein with molecular oxygen or molecular oxygen-containing gas in the presence of isobutylene and/or tertiary butanol and in the presence of a catalyst having a heteropolyacid structure represented by the following general formula:

$$Mo_aV_bP_cX_dO_e$$

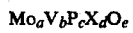

wherein Mo, V, P, and O represent molybdenum, vanadium, phosphorus, and oxygen respectively, X represents the coexistence of copper and aresenic and the a, b, c, d and e represent the atomic ratio of the elements where:
a is 10,
b is a number of 6 or less excluding 0,
c is a number of 0.5 to 6,
d is a number of 3 or less excluding 0, and
e is a number determined depending on the valance and atomic ratio of the other elements.

7 Claims, No Drawings

PROCESS FOR PRODUCING METHACRYLIC ACID

This application is a continuation of application Ser. No. 130,130, filed Mar. 13, 1980, now abandoned.

DETAILED DESCRIPTION OF THE INVENTION

This invention relates to a process for producing methacrylic acid by vapor phase oxidation of methacrolein. It relates more specifically to a process for producing methacrylic acid by catalytic vapor phase oxidation of methacrolein in the presence of isobutylene and/or tertiary butanol.

It has been known that methacrylic acid can be prepared in two stages from isobutylene or tertiary butanol by the oxidation of isobutylene or tertiary butanol to methacrolein over a proper catalyst and the successive oxidation of methacrolein to methacrylic acid over another catalyst. Many processes and catalysts for each or both stages have been proposed, but industrial practice of this process has not yet been attained in contrast to the process for producing acrylic acid by similar catalytic oxidation of propylene. The reason is considered to be mainly due to the difficulty in the oxidation of methacrolein to methacrylic acid. That is, the yield of methacrylic acid is not so high compared to that of acrylic acid in the oxidation of acrolein, the life of the catalyst is too short to maintain its activity for a long term and the like.

One of the inventors of the present application tried to improve such disadvantages in the oxidation step of methacrolein, found the catalysts having heteropolyacid structure or mixed structure of heteropolyacid and heteropolyacid salt that contain Mo, V, P, O plus additional elements have very long catalyst life and give methacrylic acid in very high yield, and proposed some processes (U.S. Pat. No. 4,172,051, etc.)

The inventors accomplished this invention by finding that the coexistence of isobutylene or tertiary butanol increases the yield of methacrylic acid in the catalytic vapor phase oxidation of methacrolein.

This invention relates to a process for producing methacrylic acid by oxidizing methacrolein under the coexistence of isobutylene or tertiary butanol with molecular oxygen or molecular oxygen-containing gas in the vapor phase over a catalyst having the following general formula:

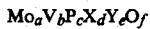
$$Mo_aV_bP_cX_dY_eO_f$$

wherein Mo, V, P and O represent molybdenum, vanadium, phosphorus and oxygen, respectively, X represents one or more elements selected from the group consisting of copper, tin, thorium, germanium, nickel, iron, cobalt, zinc, titanium, lead, rhenium, zirconium, cerium, bismuth and arsenic, Y represents one or more elements selected from the group consisting of potassium, rubidium, cesium and thallium and a, b, c, d, e and f represent the atomic ratio of the elements where a is 10,
b is a number of 6 or less than 6 excluding 0 and preferably, 0.5 to 3,
c is a number of 0.5 to 6 and preferably, 0.5 to 3,
d is a number of 3 or less than 3 excluding 0 and preferably, 0.01 to 1,
e is a number of 0 to 3 and preferably, 0.01 to 1.5,
f is a number determined depending on the valency and atomic ratio of other elements and is usually a number of 32 to 80.

The preferred components of X include copper, arsenic, tin, germanium, nickel, rhenium, zirconium, cerium and bismuth. The most preferred catalysts are those which contain both copper and arsenic.

As mentioned above, this invention is based on the discovery of the preferred effect of isobutylene or tertiary butanol that its coexistence increases the yield of methacrylic acid in the vapor phase oxidation of methacrolein over the specified catalysts.

As described in Japanese Patent Laying-Open Publication No. 111017/75, No. 48609/76 etc., isobutylene has been thought to have undesirable effect on the catalyst performance of heteropolyacid or its salt of molybdenum containing phosphorus as the central atom. Therefore, for the synthesis of methacrylic acid from isobutylene via methacrolein, the process which comprises the separation and purification of methacrolein before its oxidation has been proposed.

It is an object of this invention to provide a novel method for the production of methacrylic acid by catalytic vapor phase oxidation of methacrolein wherein the coexistence of isobutylene or tertiary butanol in the feed increases the yield of methacrylic acid, but as an additional effect of this invention, the effluent gas containing methacrolein obtained by the catalytic oxidation of isobutylene or tertiary butanol can be used as the feed of methacrolein oxidation process without separating unreacted isobutylene in the two stage oxidation of isobutylene or tertiary butanol to methacrylic acid via methacrolein.

The novel effect of this invention can only be attained when the specified catalysts mentioned above are used. The catalyst of this invention can be prepared by generally known methods for preparing usual oxide catalysts or catalysts having heteropoly acid structure or heteropoly acid salt structure.

There is no limitation to select starting materials for the preparation of the catalyst and various materials can be used. Possible starting materials for molybdenum include molybdenum oxide, molybdic acid, phosphomolybdic acid, ammonium molybdate etc.; those for vanadium include vanadium oxide, ammonium vanadate etc.; those for phosphorus include phosphoric acid, phosphorus acid, phosphorus pentoxide, etc,; those for X and Y include their nitrates, sulfates, carbonates, organic acid salts, halides, hydroxides, oxides, etc.

The catalyst of this invention can be prepared, for example, by reacting the starting materials for the constituent elements in water or in an organic solvent under heating, evaporating to dryness and if necessary, calcining the dried product. In case calcination is required, the calcination temperature is preferably in the range of 200°–500° C. and more preferably in the range of 250°–430° C.

Though the catalyst of this invention shows high catalytic activity without being supported on any carriers, preferable effects such as improvements in thermal stability and catalyst life and increase in the yield of methacrylic acid can be expected by supporting it on a suitable carrier. Preferred carriers include silicon carbide, fused alumina, α-alumina, aluminum powder, diatomaceous earth, titanium oxide and the like.

From the point of view of the structure of the catalyst, the preferred catalyst in this invention is one which has heteropoly acid structure or mixed structure of heteropoly acid and heteropoly acid salt. The basic structure of the catalyst is phosphovanadomolybdic acid and other additional elements are considered to be fixed in the structure of the heteropoly acid by partly replacing its constituent elements and contribute to the improvement in catalytic activity and selectivity as well as in the stability of the structure. The catalyst having such heteropoly acid structure or mixed structure of heteropoly acid and heteropoly acid salts has very long catalyst life. The heteropoly acid structure can be identified by the characteristic X ray diffraction peaks observed at $2\theta = 8.0°$, $8.9°$, $9.3°$, etc. In the case of mixed structure of heteropoly acid and heteropoly acid salt, X ray diffraction peaks at $2\theta = 26.6°$, $10.8°$, etc. characteristic for heteropoly acid salt can also be observed in addition to the peaks of heteropoly acid.

The catalyst having heteropoly acid structure or mixed structure of heteropoly acid and heteropoly acid salt can be readily prepared by general methods for preparing heteropoly acid or heteropoly acid salt, but it should be noted to avoid the formation of heteropoly acid ammonium salt in the resultant catalyst. Particularly preferred methods include those such as dispersing or dissolving the starting materials, for example, phosphoric acid and oxides or phosphates of the constituent elements into water, reacting the same under heating, removing insoluble component, if necessary, and then evaporating the solution to dryness or reacting phosphovanadomolybdic acid with oxides, hydroxides, phosphates, carbonates and the like of the remaining components.

In practicing the invention, isobutylene or tertiary butanol is added to the feed preferably in the range of 0.1–30% based on mole fraction of methacrolein and isobutylene or tertiary butanol and desirable effects can be expected especially in the range of 1–10%. It should be noted that isobutylene and tertiary butanol added are partly converted to methacrylic acid. However, even if all of isobutylene or tertiary butanol were assumed to be converted to methacrylic acid, though impossible, the yield of methacrylic acid from methacrolein is still estimated to be higher than in the reaction without isobutylene or tertiary butanol. This fact gives the evidence of the increase in selectivity of methacrylic acid from methacrolein with coexistence of isobutylene or tertiary butanol.

In the process of this invention, isobutylene or tertiary butanol may be added to the feed containing methacrolein, which is then introduced to the reactor or the effluent gas containing methacrolein and isobutylene obtained by the catalytic oxidation of isobutylene or tertiary butanol may be used as the feed of this invention. In the latter case the amount of isobutylene in the effluent gas can be adjusted by controlling the conversion of isobutylene.

The amount of molecular oxygen in the feed of this invention will generally be between 0.5 to 20 moles, preferably 1 to 10 moles of oxygen per mole of methacrolein and isobutylene or tertiary butanol added. It is preferable for smooth reaction to add 1 to 20 moles of steam per mole of methacrolein and isobutylene or tertiary butanol to the feed. The reactant feed may further contain other inert gases, for example, nitrogen, carbon oxides, saturated hydrocarbons and the like.

The reaction of this invention is carried out at temperatures of preferably 250° to 400° C. and more preferably 250° to 360° C. The pressure is preferably around atmospheric, but may be superatmospheric or subatmospheric, if desired. The preferred pressure is 1 to 5 atm. The space velocity may vary from about 100 to 6000 $hr^{-1}$ (NTP) and preferably from 500 to 3000 $hr^{-1}$.

In the examples no particular references are made to the details of oxygen in the catalyst composition since they are determined in accordance with the atomic ratio and valency of other elements.

Conversion (Conv.) selectivity (Select.) and yield are defined as follows:

$$\text{Conv. (\%)} = \left(1 - \frac{\text{moles of methacrolein unreacted}}{\begin{array}{c}\text{total moles of methacrolein,}\\\text{isobutylene and tertiary}\\\text{butanol fed}\end{array}}\right) \times 100$$

$$\text{Yield (\%)} = \frac{\text{moles of methacrylic acid formed}}{\begin{array}{c}\text{total moles of methacrolein,}\\\text{isobutylene and tertiary butanol fed}\end{array}} \times 100$$

$$\text{Select. (\%)} = \frac{\text{Yield}}{\text{Conv.}} \times 100$$

EXAMPLE 1

100 g of molybdenum trioxide, 6.3 g vanadium pentoxide, 1.1 g of copper oxide and 8.0 g of orthophosphoric acid were dispersed or dissolved in 1000 ml of deionized water. The resultant mixture was boiled and refluxed with stirring for about 6 hours to produce a clear orange red solution. After removing a slight amount of insoluble contents, it was evaporated to dryness on a hot bath. The dried products thus obtained (catalyst) had a composition: $Mo_{10}V_1P_1Cu_{0.2}$ and was confirmed to be heteropoly acid by the observation of X-ray diffraction peaks at $2\theta = 8.0°$, $8.9°$, $9.3°$ and the like. The catalyst was ground to 24–48 mesh and 10 ml of it was packed in a tubular reactor made of pyrex glass of 18 mm in inside diameter and the reactor was immersed in a fluidized bath. A gaseous mixture composed of 0.475 l/hr of methacrolein, 0.025 l/hr of isobutylene, 1.5 l/hr of oxygen, 8.0 l/hr of nitrogen and 5.0 l/hr of steam was introduced into the reactor and subjected to oxidation reaction. The result is shown in Table 1.

EXAMPLES 2–15

1.1 g of copper oxide in Example 1 was replaced in each of the examples with 1.6 g of tin oxide, 3.7 g of thorium oxide, 1.4 g of germanium oxide, 1.0 g of nickel oxide, 1.1 g of iron oxide, 1.1 g of cobalt oxide, 1.1 g of zinc oxide, 1.1 g of titanium oxide, 3.2 g of trilead tetroxide, 3.4 g of rhenium oxide, 1.7 g of zirconium oxide, 2.4 g of cerium oxide, 3.2 g of bismuth oxide and 1.9 g of arsenic acid respectively and dried products (catalysts) having compositions as shown in Table 1 were obtained. Then the oxidation reactions were carried out using the above catalysts under the same reaction conditions as in Example 1. The results are shown in Table 1.

All of the dried products (catalysts) were confirmed to be heteropoly acid by the observation of X-ray diffraction peaks at $2\theta = 8.0°$, $8.9°$, $9.3°$ and the like.

EXAMPLES 16–22

The dried products (catalysts) as shown in Table 1 were prepared under identical conditions as in Example 1. The oxidation reactions were carried out using the above catalysts under the same reaction conditions as in Example 1. The results are shown in Table 1.

These catalysts were confirmed to be heteropoly acid by the observation of X-ray diffraction peaks at $2\theta = 8.0°$, $8.9°$, $9.3°$ and the like.

COMPARATIVE EXAMPLES 1–22

The procedures of Examples 1–22 were repeated except that isobutylene was not introduced into the reactor. The results are shown in Table 1.

COMPARATIVE EXAMPLES 1′–22′

The procedures of Examples 1–22 were repeated except that methacrolein was not introduced into the reactor. The results are shown in Table 1.

The flow rate of methacrylic acid produced in Example 1 is higher than sum of those in separative oxidation of methacrolein and isobutylene (Comparative Example 1 and 1′), which verifies the effect of the coexistence of isobutylene. The same comparison was done in all examples to show the effect.

TABLE 1

|  | Catalyst Composition | Flow Rate (l/hr) MAL | Flow Rate (l/hr) IB | RT (°C.) | Conv. (%) | Select. (%) | Yield (%) | Flow Rate of MAA formed (l/hr) |
|---|---|---|---|---|---|---|---|---|
| E 1 | $Mo_{10}V_1P_1Cu_{0.2}$ | 0.475 | 0.025 | 320 | 94.5 | 78.8 | 74.5 | 0.373 |
| CE 1 | ″ | 0.475 | 0 | ″ | 95.0 | 75.9 | 72.1 | 0.342 |
| CE 1′ | ″ | 0 | 0.025 | ″ | 90.0 | 67.2 | 60.5 | 0.015 |
| E 2 | $Mo_{10}V_1P_1Sn_{0.2}$ | 0.475 | 0.025 | 330 | 93.8 | 75.0 | 70.4 | 0.352 |
| CE 2 | ″ | 0.475 | 0 | ″ | 94.3 | 73.3 | 69.1 | 0.328 |
| CE 2′ | ″ | 0 | 0.025 | ″ | 88.7 | 65.1 | 57.7 | 0.014 |
| E 3 | $Mo_{10}V_1P_1Th_{0.2}$ | 0.475 | 0.025 | 325 | 93.0 | 75.4 | 70.1 | 0.351 |
| CE 3 | ″ | 0.475 | 0 | ″ | 93.8 | 73.5 | 68.9 | 0.327 |
| CE 3′ | ″ | 0 | 0.025 | ″ | 88.3 | 65.5 | 57.8 | 0.014 |
| E 4 | $Mo_{10}V_1P_1Ge_{0.2}$ | 0.475 | 0.025 | 325 | 93.5 | 75.5 | 70.6 | 0.353 |
| CE 4 | ″ | 0.475 | 0 | ″ | 93.7 | 75.0 | 70.3 | 0.334 |
| CE 4′ | ″ | 0 | 0.025 | ″ | 89.5 | 65.0 | 58.2 | 0.015 |
| E 5 | $Mo_{10}V_1P_1Ni_{0.2}$ | 0.475 | 0.025 | 330 | 92.8 | 76.1 | 70.6 | 0.353 |
| CE 5 | ″ | 0.475 | 0 | ″ | 93.5 | 74.5 | 69.7 | 0.331 |
| CE 5′ | ″ | 0 | 0.025 | ″ | 86.5 | 64.5 | 55.8 | 0.014 |
| E 6 | $Mo_{10}V_1P_1Fe_{0.2}$ | 0.475 | 0.025 | 320 | 92.5 | 77.9 | 72.1 | 0.361 |
| CE 6 | ″ | 0.475 | 0 | ″ | 93.2 | 76.0 | 70.8 | 0.336 |
| CE 6′ | ″ | 0 | 0.025 | ″ | 88.8 | 65.5 | 58.2 | 0.015 |
| E 7 | $Mo_{10}V_1P_1Co_{0.2}$ | 0.475 | 0.025 | 330 | 91.1 | 77.4 | 70.5 | 0.353 |
| CE 7 | ″ | 0.475 | 0 | ″ | 92.1 | 74.4 | 68.5 | 0.325 |
| CE 7′ | ″ | 0 | 0.025 | ″ | 86.1 | 64.9 | 55.9 | 0.014 |
| E 8 | $Mo_{10}V_1P_1Zn_{0.2}$ | 0.475 | 0.025 | 330 | 92.9 | 75.5 | 70.1 | 0.351 |
| CE 8 | ″ | 0.475 | 0 | ″ | 94.0 | 73.1 | 68.7 | 0.326 |
| CE 8′ | ″ | 0 | 0.025 | ″ | 86.9 | 63.5 | 55.2 | 0.014 |
| E 9 | $Mo_{10}V_1P_1Ti_{0.2}$ | 0.475 | 0.025 | 325 | 94.3 | 76.1 | 71.8 | 0.359 |
| CE 9 | ″ | 0.475 | 0 | ″ | 95.1 | 74.7 | 71.0 | 0.337 |
| CE 9′ | ″ | 0 | 0.025 | ″ | 89.1 | 64.1 | 57.1 | 0.014 |
| E 10 | $Mo_{10}V_1P_1Pb_{0.2}$ | 0.475 | 0.025 | 330 | 92.5 | 76.8 | 71.0 | 0.355 |
| CE 10 | ″ | 0.475 | 0 | ″ | 92.8 | 74.5 | 69.1 | 0.328 |
| CE 10′ | ″ | 0 | 0.025 | ″ | 88.7 | 62.1 | 55.1 | 0.014 |
| E 11 | $Mo_{10}V_1P_1Re_{0.2}$ | 0.475 | 0.025 | 320 | 93.1 | 77.1 | 71.8 | 0.359 |
| CE 11 | ″ | 0.475 | 0 | ″ | 93.5 | 75.1 | 70.2 | 0.333 |
| CE 11′ | ″ | 0 | 0.025 | ″ | 85.2 | 62.8 | 53.5 | 0.013 |
| E 12 | $Mo_{10}V_1P_1Zr_{0.2}$ | 0.475 | 0.025 | 330 | 94.0 | 75.9 | 71.3 | 0.357 |
| CE 12 | ″ | 0.475 | 0 | ″ | 95.1 | 73.6 | 70.0 | 0.333 |
| CE 12′ | ″ | 0 | 0.025 | ″ | 87.8 | 63.2 | 55.5 | 0.014 |
| E 13 | $Mo_{10}V_1P_1Ce_{0.2}$ | 0.475 | 0.025 | 325 | 93.1 | 77.3 | 72.0 | 0.360 |
| CE 13 | ″ | 0.475 | 0 | ″ | 93.7 | 75.2 | 70.5 | 0.335 |
| CE 13′ | ″ | 0 | 0.025 | ″ | 86.6 | 65.9 | 57.1 | 0.014 |
| E 14 | $Mo_{10}V_1P_1Bi_{0.2}$ | 0.475 | 0.025 | 330 | 93.1 | 76.0 | 70.8 | 0.354 |
| CE 14 | ″ | 0.475 | 0 | ″ | 94.0 | 73.1 | 68.7 | 0.326 |
| CE 14′ | ″ | 0 | 0.025 | ″ | 87.9 | 63.4 | 55.7 | 0.014 |
| E 15 | $Mo_{10}V_1P_1As_{0.2}$ | 0.475 | 0.025 | 330 | 94.1 | 76.5 | 72.0 | 0.360 |
| CE 15 | ″ | 0.475 | 0 | ″ | 94.5 | 74.6 | 70.5 | 0.335 |
| CE 15′ | ″ | 0 | 0.025 | ″ | 87.0 | 65.5 | 57.0 | 0.014 |
| E 16 | $Mo_{10}V_1P_1Cu_{0.2}As_{0.2}$ | 0.475 | 0.025 | 320 | 93.0 | 86.0 | 80.0 | 0.400 |
| CE 16 | ″ | 0.475 | 0 | ″ | 93.4 | 83.6 | 78.1 | 0.371 |
| CE 16′ | ″ | 0 | 0.025 | ″ | 85.2 | 70.1 | 59.7 | 0.015 |
| E 17 | $Mo_{10}V_1P_1Cu_{0.2}Sn_{0.2}$ | 0.475 | 0.025 | 320 | 93.8 | 82.1 | 77.0 | 0.385 |
| CE 17 | ″ | 0.475 | 0 | ″ | 94.5 | 79.5 | 75.1 | 0.357 |
| CE 17′ | ″ | 0 | 0.025 | ″ | 90.1 | 64.6 | 58.2 | 0.015 |
| E 18 | $Mo_{10}V_1P_1Cu_{0.2}Ge_{0.2}$ | 0.475 | 0.025 | 320 | 95.0 | 80.1 | 76.1 | 0.381 |
| CE 18 | ″ | 0.475 | 0 | ″ | 95.5 | 78.0 | 74.5 | 0.354 |
| CE 18′ | ″ | 0 | 0.025 | ″ | 89.1 | 67.2 | 59.9 | 0.015 |
| E 19 | $Mo_{10}V_1P_1Cu_{0.2}Ce_{0.2}$ | 0.475 | 0.025 | 320 | 92.5 | 80.5 | 74.5 | 0.373 |
| CE 19 | ″ | 0.475 | 0 | ″ | 93.8 | 78.7 | 73.8 | 0.351 |
| CE 19′ | ″ | 0 | 0.025 | ″ | 87.5 | 65.4 | 57.2 | 0.014 |
| E 20 | $Mo_{10}V_1P_1Cu_{0.2}Zr_{0.2}$ | 0.475 | 0.025 | 320 | 95.0 | 81.2 | 77.1 | 0.386 |
| CE 20 | ″ | 0.475 | 0 | ″ | 95.7 | 78.9 | 75.5 | 0.359 |
| CE 20′ | ″ | 0 | 0.025 | ″ | 91.0 | 65.4 | 59.5 | 0.015 |
| E 21 | $Mo_{10}V_1P_1Ni_{0.2}As_{0.2}$ | 0.475 | 0.025 | 330 | 93.3 | 78.8 | 73.5 | 0.368 |
| CE 21 | ″ | 0.475 | 0 | ″ | 94.1 | 77.5 | 72.9 | 0.0346 |
| CE 21′ | ″ | 0 | 0.025 | ″ | 85.1 | 63.6 | 54.1 | 0.014 |
| E 22 | $Mo_{10}V_1P_1Ge_{0.1}Sn_{0.1}$ | 0.475 | 0.025 | 330 | 94.1 | 77.0 | 72.5 | 0.363 |

TABLE 1-continued

|  | Catalyst Composition | Flow Rate (l/hr) MAL | IB | RT (°C.) | Conv. (%) | Select. (%) | Yield (%) | Flow Rate of MAA formed (l/hr) |
| --- | --- | --- | --- | --- | --- | --- | --- | --- |
| CE 22 | " | 0.475 | 0 | " | 95.3 | 74.6 | 71.1 | 0.338 |
| CE 22' | " | 0 | 0.025 | " | 86.0 | 63.7 | 54.8 | 0.014 |

In this Table and in Tables 2-5,
E represents Example,
Ce represents Comparative Example,
MAL represents methacrolein,
IB represents isobutylene,
RT represents reaction temperature,
MAA represents methacrylic acid and TBA represents tertiary butanol.

EXAMPLE 23

100 g of molybdenum trioxide, 6.3 g of vanadium pentoxide, 1.1 g of copper oxide and 8.0 g of orthophosphoric acid were dispersed or dissolved in 1000 ml of deionized water and after about 3 hours of heating and stirring of the mixture, 0.45 g of potassium hydroxide was added to the resultant solution. The mixture was refluxed for about 1 hour. The aqueous solution thus formed was evaporated to dryness on a water bath. The composition of the dried product (catalyst) was $Mo_{10}V_1P_1Cu_{0.2}K_{0.1}$.

In the X-ray diffraction pattern of the catalyst, diffraction peaks of $2\theta = 8.0°$, $8.9°$, $9.3°$, etc. due to heteropoly acid mainly composed of phosphovanadomolybdic acid and faint diffraction peaks of $2\theta = 26.6°$, $10.8°$, etc. due to the potassium salt of the heteropoly acid were recognized. The fact shows that the catalyst obtained is a mixture of heteropoly acid mainly composed of phosphovanadomolybdic acid and its potassium salt.

The oxidation reaction was carried out using the above catalyst under the same reaction conditions as in Example 1. The results are shown in Table 2.

EXAMPLES 24-30

The catalysts as shown in Table 2 were prepared as in Example 23. The oxidation reactions were carried out using the above catalysts under the same reaction conditions as in Example 1. The results are shown in Table 2.

In the X-ray diffraction pattern of the catalysts, diffraction peaks of $2\theta = 8.0°$, $8.9°$, $9.3°$, etc. due to heteropoly acid mainly composed of phosphovanadomolybdic acid and faint diffraction peaks of $2\theta = 26.6°$, $10.8°$, etc. due to the salt of the heteropoly acid were recognized. The fact shows that each of the catalysts is a mixture of the heteropoly acid mainly composed of phosphovanadomolybdic acid and its salt.

COMPARATIVE EXAMPLES 23-30

The procedures of Examples 23-30 were repeated except that isobutylene was not introduced into the reactor. The results are shown in Table 2.

COMPARATIVE EXAMPLES 23'-30'

The procedures of Examples 23-30 were repeated except that methacrolein was not introduced into the reactor. The results are shown in Table 2.

TABLE 2

|  | Catalyst Composition | Flow Rate (l/hr) MAL | IB | RT (°C.) | Conv. (%) | Select. (%) | Yield (%) | Flow Rate of MAA formed (l/hr) |
| --- | --- | --- | --- | --- | --- | --- | --- | --- |
| E 23 | $Mo_{10}V_1P_1Cu_{0.2}K_{0.1}$ | 0.475 | 0.025 | 310 | 94.5 | 79.4 | 75.0 | 0.375 |
| CE 23 | " | 0.475 | 0 | " | 95.1 | 78.7 | 74.8 | 0.355 |
| CE 23' | " | 0 | 0.025 | " | 89.1 | 68.2 | 60.8 | 0.015 |
| E 24 | $Mo_{10}V_1P_1Cu_{0.2}Rb_{0.1}$ | 0.475 | 0.025 | 310 | 91.5 | 79.6 | 72.8 | 0.364 |
| CE 24 | " | 0.475 | 0 | " | 91.9 | 78.7 | 72.3 | 0.343 |
| CE 24' | " | 0 | 0.025 | " | 87.7 | 67.3 | 59.1 | 0.015 |
| E 25 | $Mo_{10}V_1P_1Cu_{0.2}Cs_{0.1}$ | 0.475 | 0.025 | 310 | 94.0 | 79.3 | 74.5 | 0.373 |
| CE 25 | " | 0.475 | 0 | " | 94.3 | 78.6 | 74.1 | 0.352 |
| CE 25' | " | 0 | 0.025 | " | 89.0 | 67.6 | 60.2 | 0.015 |
| E 26 | $Mo_{10}V_1P_1Cu_{0.2}Tl_{0.1}$ | 0.475 | 0.025 | 310 | 92.0 | 79.3 | 73.0 | 0.365 |
| CE 26 | " | 0.475 | 0 | " | 92.3 | 78.8 | 72.7 | 0.345 |
| CE 26' | " | 0 | 0.025 | " | 89.5 | 66.3 | 59.3 | 0.015 |
| E 27 | $Mo_{10}V_1P_1Cu_{0.2}As_{0.2}K_{0.1}$ | 0.475 | 0.025 | 310 | 92.0 | 88.2 | 81.1 | 0.406 |
| CE 27 | " | 0.475 | 0 | " | 92.3 | 85.8 | 79.2 | 0.376 |
| CE 27' | " | 0 | 0.025 | " | 88.5 | 68.9 | 61.0 | 0.015 |
| E 28 | $Mo_{10}V_1P_1Ge_{0.1}Sn_{0.1}Cs_{0.2}$ | 0.475 | 0.025 | 330 | 93.2 | 76.1 | 70.9 | 0.355 |
| CE 28 | " | 0.475 | 0 | " | 94.1 | 73.9 | 69.5 | 0.330 |
| CE 28' | " | 0 | 0.025 | " | 87.2 | 66.4 | 57.9 | 0.014 |
| E 29 | $Mo_{10}V_1P_1Cu_{0.2}As_{0.2}K_{0.3}$ | 0.475 | 0.025 | 310 | 90.9 | 89.0 | 80.9 | 0.405 |
| CE 29 | " | 0.475 | 0 | " | 91.5 | 86.3 | 79.0 | 0.375 |
| CE 29' | " | 0 | 0.025 | " | 88.9 | 67.9 | 60.4 | 0.015 |
| E 30 | $Mo_{10}V_1P_1Sn_{0.2}K_{1.0}$ | 0.475 | 0.025 | 350 | 93.5 | 68.4 | 64.0 | 0.320 |
| CE 30 | " | 0.475 | 0 | " | 94.2 | 67.1 | 63.2 | 0.300 |
| CE 30' | " | 0 | 0.025 | " | 85.3 | 59.8 | 51.0 | 0.013 |

EXAMPLES 31-35

The catalysts having the composition shown in Table 3 were prepared by operating as in Example 1. Using the so obtained catalysts, the oxidation reactions were carried out under the identical conditions as in Example 1. The results are shown in Table 3.

COMPARATIVE EXAMPLES 31-35

The procedures of Examples 31-35 were repeated except that isobutylene was not introduced into the reactor. The results are shown in Table 3.

COMPARATIVE EXAMPLES 31'-35'

The procedures of Examples 31-35 were repeated except that methacrolein was not introduced into the reactor. The results are shown in Table 3.

COMPARATIVE EXAMPLES 36'-38'

The procedures of Examples 36-38 were repeated except that methacrolein was not introduced into the reactor. The results are shown in Table 4.

TABLE 4

| | Catalyst Composition | Flow Rate (l/hr) MAL | IB | $O_2$ | $N_2$ | $H_2O$ | RT (°C.) | Conv. (%) | Select. (%) | Yield (%) | Flow Rate of MAA formed (l/hr) |
|---|---|---|---|---|---|---|---|---|---|---|---|
| E 36 | $Mo_{10}V_1P_1Cu_{0.2}As_{0.2}$ | 0.49 | 0.01 | 1.5 | 8.0 | 5.0 | 320 | 93.5 | 85.0 | 79.5 | 0.398 |
| CE 36 | " | 0.49 | 0 | 1.5 | 8.0 | 5.0 | " | 93.7 | 83.5 | 78.2 | 0.383 |
| CE 36' | " | 0 | 0.01 | 1.5 | 8.0 | 5.0 | " | 87.1 | 68.3 | 59.5 | 0.006 |
| E 37 | " | 0.45 | 0.05 | 1.5 | 8.0 | 5.0 | 325 | 93.0 | 85.5 | 79.5 | 0.398 |
| CE 37 | " | 0.45 | 0 | 1.5 | 8.0 | 5.0 | 320 | 95.5 | 82.2 | 78.5 | 0.353 |
| CE 37' | " | 0 | 0.05 | 1.5 | 8.0 | 5.0 | 325 | 88.8 | 68.1 | 60.5 | 0.030 |
| E 38 | " | 0.35 | 0.15 | 1.5 | 8.0 | 5.0 | 330 | 94.0 | 78.2 | 73.5 | 0.368 |
| CE 38 | " | 0.35 | 0 | 1.5 | 8.0 | 5.0 | 320 | 94.1 | 82.9 | 78.0 | 0.273 |
| CE 38' | " | 0 | 0.15 | 1.5 | 8.0 | 5.0 | 330 | 89.2 | 67.4 | 60.1 | 0.090 |

TABLE 3

| | Catalyst Composition | Flow Rate (l/hr) MAL | IB | RT (°C.) | Conv. (%) | Select (%) | Yield (%) | Flow Rate of MAA formed (l/hr) |
|---|---|---|---|---|---|---|---|---|
| E 31 | $Mo_{10}V_1P_1Cu_{0.5}$ | 0.475 | 0.025 | 310 | 93.5 | 73.9 | 69.1 | 0.346 |
| CE 31 | " | 0.475 | 0 | " | 94.0 | 72.3 | 68.0 | 0.323 |
| CE 31' | " | 0 | 0.025 | " | 89.1 | 60.6 | 54.0 | 0.014 |
| E 32 | $Mo_{10}V_1P_1Cu_{1.0}$ | 0.475 | 0.025 | 300 | 93.1 | 70.4 | 65.5 | 0.328 |
| CE 32 | " | 0.475 | 0 | " | 93.8 | 68.2 | 64.0 | 0.304 |
| CE 32' | " | 0 | 0.025 | " | 88.1 | 57.9 | 51.0 | 0.013 |
| E 33 | $Mo_{10}V_1P_3Cu_{0.3}$ | 0.475 | 0.025 | 320 | 94.1 | 74.6 | 70.2 | 0.351 |
| CE 33 | " | 0.475 | 0 | " | 94.5 | 73.5 | 69.5 | 0.330 |
| CE 32' | " | 0 | 0.025 | " | 87.0 | 63.2 | 55.0 | 0.014 |
| E 34 | $Mo_{10}V_{0.5}P_1Cu_{0.2}$ | 0.475 | 0.025 | 310 | 92.1 | 75.7 | 69.7 | 0.349 |
| CE 34 | " | 0.475 | 0 | " | 93.1 | 74.1 | 69.0 | 0.328 |
| CE 34' | " | 0 | 0.025 | " | 85.0 | 62.4 | 53.0 | 0.013 |
| E 35 | $Mo_{10}V_2P_1Cu_{0.2}As_{0.2}$ | 0.475 | 0.025 | 320 | 93.5 | 83.6 | 78.2 | 0.391 |
| CE 35 | " | 0.475 | 0 | " | 93.8 | 82.1 | 77.0 | 0.366 |
| CE 35' | " | 0 | 0.025 | " | 90.1 | 64.5 | 58.1 | 0.015 |

EXAMPLES 36-38

Using the catalyst prepared as in Example 16, the oxidation reactions were carried out in a similar manner as in Example 1 but varying the flow rate of isobutylene. The results are shown in Table 4.

COMPARATIVE EXAMPLES 36-38

The procedures of Examples 36-38 were repeated except that isobutylene was not introduced into the reactor. The results are shown in Table 4.

EXAMPLES 39-41

Using the catalysts prepared as in Example 1, 16 and 27, the oxidation reactions were carried out under the same conditions as in Example 1 except that tertiary butanol was introduced into the reactor instead of isobutylene. The results are shown in Table 5.

COMPARATIVE EXAMPLES 39-41

The procedures of Examples 39-41 were repeated except that tertiary butanol was not introduced into the reactor. The results are shown in Table 5.

COMPARATIVE EXAMPLES 39'-41'

The procedures of Examples 39-41 were repeated except that methacrolein was not introduced into the reactor. The results are shown in Table 5.

TABLE 5

| | Catalyst Composition | Flow Rate (l/hr) MAL | TBA | $O_2$ | $N_2$ | $H_2O$ | RT (°C.) | Conv. (%) | Select. (%) | Yield (%) | Flow Rate of MAA formed (l/hr) |
|---|---|---|---|---|---|---|---|---|---|---|---|
| E 39 | $Mo_{10}V_1P_1Cu_{0.2}$ | 0.475 | 0.025 | 1.5 | 8.0 | 5.0 | 320 | 94.3 | 79.0 | 74.5 | 0.373 |
| CE 39 | " | 0.475 | 0 | 1.5 | 8.0 | 5.0 | " | 95.0 | 75.9 | 72.1 | 0.342 |
| CE 39' | " | 0 | 0.025 | 1.5 | 8.0 | 5.0 | " | 90.5 | 67.2 | 60.8 | 0.015 |
| E 40 | $Mo_{10}V_1P_1Cu_{0.2}As_{0.2}$ | 0.475 | 0.025 | 1.5 | 8.0 | 5.0 | 320 | 93.3 | 86.0 | 80.2 | 0.401 |
| CE 40 | " | 0.475 | 0 | 1.5 | 8.0 | 5.0 | " | 93.4 | 83.6 | 78.1 | 0.371 |
| CE 40' | " | 0 | 0.025 | 1.5 | 8.0 | 5.0 | " | 85.5 | 69.9 | 59.8 | 0.015 |
| E 41 | $Mo_{10}V_1P_1Cu_{0.2}As_{0.2}K_{0.1}$ | 0.475 | 0.025 | 1.5 | 8.0 | 5.0 | 310 | 92.3 | 88.3 | 81.5 | 0.408 |
| CE 41 | " | 0.475 | 0 | 1.5 | 8.0 | 5.0 | " | 92.3 | 85.8 | 79.2 | 0.376 |

TABLE 5-continued

| Catalyst Composition | Flow Rate (l/hr) MAL | TBA | $O_2$ | $N_2$ | $H_2O$ | RT (°C.) | Conv. (%) | Select. (%) | Yield (%) | Flow Rate of MAA formed (l/hr) |
|---|---|---|---|---|---|---|---|---|---|---|
| CE 41' " | 0 | 0.025 | 1.5 | 8.0 | 5.0 | " | 88.7 | 69.0 | 61.2 | 0.015 |

EXAMPLE 42

The procedure of Example 39 was repeated respectively using the same catalyst as those used in Examples 2-15, 17-26 and 28-30.

In all cases, almost same results were obtained as in Examples 2-15, 17-26 and 28-30 and the effect of coexistence of tertiary butanol was observed.

What we claim is:

1. A process for producing methacrylic acid by vapor phase oxidation of methacrolein with molecular oxygen or molecular oxygen-containing gas in the presence of isobutylene and/or tertiary butanol and in the presence of a catalyst having heteropoly acid structure and represented by the following general formula:

$$Mo_a V_b P_c X_d O_f$$

wherein Mo, V, P and O represent molybdenum, vanadium, phosphorus and oxygen, respectively, X represents the coexistence of copper and arsenic, and a, b, c, d, and f represent the atomic ratio of the elements where a is 10, b is a number of 6 or less than 6 excluding 0,
c is a number of 0.5 to 6,
d is a number of 3 or less than 3 excluding 0,
f is a number determined depending on the valancy and atomic ratio of other elements.

2. The process of claim 1 wherein the atomic ratio a is 10, b is a number of 0.5 to 3, c is a number of 0.5 to 3 and d is a number of 0.01 to 1.

3. The process of claim 1 or 2 wherein the amount of isobutylene and/or tertiary butanol added to the feed is in the range of 0.1 to 30% based on mole fraction of methacrolein and isobutylene and/or tertiary butanol.

4. The process of claim 1 or 2 wherein the oxidation reaction temperature is 250° to 400° C. and the space velocity is 100 to 6000 $hr^{-1}$.

5. The process of claim 1 or 2 wherein the oxidation reaction temperature is 250° to 360° C. and the space velocity is 500 to 3000 $hr^{-1}$.

6. The process of claim 1 or 2 wherein the molar ratio of oxygen to methacrolein and isobutylene and/or tertiary butanol is 0.5 to 20.

7. The process of claim 1 or 2 wherein the reaction is carried out in the presence of steam.

* * * * *